United States Patent [19]
Goto et al.

[11] Patent Number: 6,025,348
[45] Date of Patent: Feb. 15, 2000

[54] OIL AND FAT COMPOSITION CONTAINING PHYTOSTEROL

[75] Inventors: Naohiro Goto; Tsutomu Nishide; Yukitaka Tanaka; Takuji Yasukawa, all of Ibaraki, Japan

[73] Assignee: Kao Corporation, Tokyo, Japan

[21] Appl. No.: 09/069,754

[22] Filed: Apr. 30, 1998

[51] Int. Cl.[7] .......................... A61K 31/56; A61K 31/235
[52] U.S. Cl. ........................... 514/182; 514/533; 514/824
[58] Field of Search ..................................... 514/182, 533, 514/824

[56] References Cited

U.S. PATENT DOCUMENTS

| | | | |
|---|---|---|---|
| 3,862,197 | 1/1975 | Castner | 260/418 |
| 4,976,984 | 12/1990 | Yasukawa et al. | 426/602 |
| 5,843,499 | 12/1998 | Moreau et al. | 426/2 |

FOREIGN PATENT DOCUMENTS

| | | |
|---|---|---|
| 0 191 217 | 8/1986 | European Pat. Off. . |
| 289 636 | 11/1988 | European Pat. Off. . |
| 0 307 154 | 3/1989 | European Pat. Off. . |
| 0 426 155 | 5/1991 | European Pat. Off. . |
| 0 378 893 | 7/1992 | European Pat. Off. . |
| 495 510 | 7/1992 | European Pat. Off. . |
| 0 307 154 B2 | 4/1996 | European Pat. Off. . |
| 0 836 805 | 4/1998 | European Pat. Off. . |
| 839 458 | 5/1998 | European Pat. Off. . |
| 56-14087 | 4/1981 | Japan . |
| 57-39736 | 3/1982 | Japan . |
| 57-26732 | 6/1982 | Japan . |
| 57-206336 | 12/1982 | Japan . |
| 61-15647 | 1/1986 | Japan . |
| 62-148424 | 7/1987 | Japan . |
| 1-174384 | 7/1989 | Japan . |
| 2-190146 | 7/1990 | Japan . |
| 6-506909 | 8/1994 | Japan . |
| 6-59164 | 8/1994 | Japan . |
| 6-65311 | 8/1994 | Japan . |
| 10-75898 | 3/1998 | Japan . |
| 10-85576 | 3/1998 | Japan . |
| 10-179086 | 7/1998 | Japan . |
| 133567 | 9/1987 | U.S.S.R. . |
| WO 96/23425 | 8/1996 | WIPO . |
| WO 96/38047 | 12/1996 | WIPO . |
| WO 97/42830 | 11/1997 | WIPO . |
| WO 98/01461 | 1/1998 | WIPO . |
| WO 98/06405 | 2/1998 | WIPO . |
| WO 98/19556 | 5/1998 | WIPO . |

OTHER PUBLICATIONS

Patent Abstracts of Japan, vol. 015, No. 068(C–0807), Feb. 18, 1991, JP 02 295490, Dec. 6, 1990.

Patent Abstracts of Japan, vol. 017, No. 429(C–1095), Aug. 10, 1993, JP 05 095792, Apr. 20, 1993.

Xavier Pelleter, et al., "A Diet Moderately Enriched In Phytosterols Lowers Plasma Cholesterol Concentrations In Normocholesterolemic Humans", Ann Nutr Metab 1995;39:291–295.

*Primary Examiner*—Kimberly Jordan
*Attorney, Agent, or Firm*—Oblon, Spivak, McClelland, Maier & Neustadt, P.C.

[57] ABSTRACT

An oil/fat composition is provided which lowers the blood cholesterol level of a person having a high cholesterol level when used in daily life similarly to ordinary fats and is usable without posing any problem concerning appearance, flavor, heat cooking, etc. as compared with generally edible fats, wherein the oil/fat composition contains a phytosterol contained in an oil/fat containing one or more polyhydric alcohol/fatty acid esters each having a degree of esterification of 2 or higher and containing at least one hydroxyl group remaining unesterified.

14 Claims, No Drawings

OIL AND FAT COMPOSITION CONTAINING PHYTOSTEROL

BACKGROUND OF THE INVENTION

1. Field of the Invention

The present invention relates to an oil and fat composition which, when used in daily life similarly to ordinary fats, can lower the blood cholesterol level of a person having a high cholesterol level. It further relates to a food and a pharmaceutical preparation each containing the oil and fat composition.

2. Discussion of the Background

There are many drugs and food materials which lower the blood cholesterol level and are highly effective in prophylaxis and therapy. However, since these substances are used in the form of a medicine or auxiliary nutrient food, they should be ingested while paying attention to control of the blood cholesterol level of the subject ingesting them.

Among the components effective in lowering blood cholesterol are phytosterols. Phytosterols are contained in plant seeds in large amounts and are contained in ordinary edible vegetable oils in amounts of about 0.1 to 1.0% by weight. Many investigations have been made on the blood cholesterol lowering effect of phytosterols. It has been reported that the daily phytosterol ingestion necessary for significantly lowering the blood cholesterol level is 236 mg to 18 g per day (e.g., *Ann. Nutr. Metab.*, 39, 291, 1995).

For heightening the blood cholesterol lowering effect of a phytosterol, it is effective to dissolve the phytosterol in a fat, such as an edible oil. When the phytosterol dissolved in a fat is ingested, it effectively functions to form micelles in the small intestine competitively with cholesterol and, as a result, the absorption of cholesterol is inhibited.

With respect to foods containing a fat and a phytosterol, "Fat Food Lowering Blood Cholesterol" (L C Liebens; WO 96/38047), for example, discloses a food comprising a natural fat containing tocotrienol and a phytosterol and/or oryzanol; "Process for Producing Edible Fat Composition" (L J Janduck; JP-B 57-26732) discloses an edible oil containing a phytosterol dissolved therein, with the aid of a free fatty acid as a solubilizing agent, in an amount sufficient for imparting a significant cholesterol lowering activity; and "Edible Fat" (Kobayashi et al.; JP-A 57-206336) discloses an edible liquid fat containing vitamin E and a phytosterol in large amounts. Furthermore, "Substance for Lowering High Cholesterol Level in Blood Serum and Process for Preparing the Substance" (Miettinen et al.; JP-A 6-506909) discloses the use of a β-sitostanol/fatty acid ester.

SUMMARY OF THE INVENTION

Accordingly, one object of the present invention is to provide an oil and fat composition which lowers the blood cholesterol level of a person having a high cholesterol level when ingested in daily life similarly to ordinary fats and is usable without posing any problem concerning appearance, flavor, heat cooling, etc. when compared with general edible fats.

Another object of the invention is to provide a pharmaceutical preparation or food containing the fat composition.

These and other objects of the present invention have been satisfied by the discovery of an oil and fat composition obtained by dissolving a phytosterol in a fat comprising one or more specific polyhydric alcohol/fatty acid esters and its use in a manner similar to ordinary edible fats that enables a blood cholesterol concentration to be lowered.

DESCRIPTION OF THE PREFERRED EMBODIMENTS

The present invention relates to a fat composition obtained by dissolving a phytosterol in a fat comprising one or more polyhydric alcohol/fatty acid esters each having a degree of esterification of 2 or higher and containing at least one hydroxyl group remaining unesterified.

The invention thus provides (1) an oil and fat composition comprising the polyhydric alcohol/fatty acid ester and phytosterol, (2) a method for dissolving phytosterol with an effective amount of the polyhydric alcohol/fatty acid ester, (3) a method for decreasing an amount in blood of cholesterols by administering an effective amount of the polyhydric alcohol/fatty acid ester and an effective amount of phytosterol to a subject in need thereof, (4) a food product comprising the polyhydric alcohol/fatty acid ester and phytosterol, (5) a frying oil comprising the polyhydric alcohol/fatty acid ester and phytosterol and (6) a pharmaceutical composition comprising a pharmacologically effective amount of the polyhydric alcohol/fatty acid ester, phytosterol and a pharmacologically acceptable carrier.

It is preferred to mix the polyhydric alcohol/fatty acid ester with phytosterol and heat the mixture to obtain the product composition.

It is also preferred that the polyhydric alcohol has at least three alcoholic hydroxy groups, i.e., is three- or more valent.

While not wanting to be bound to any particular mechanism of action, it is believed that when a phytosterol is ingested together with cholesterol, competitive miclle formation occurs in the small intestine to reduce cholesterol absorption into the body and thus lower the blood cholesterol level. It is therefore important that for heightening the micelle fornation by a phytosterol in the small intestine, the phytosterol be dissolved in a fat to be ingested.

As a result, the present invention uses a polyhydric alcohol/fatty acid ester having a degree of esterification (the number of csterified hydroxyl groups) of 2 or higher and containing at least one hydroxyl group remaining unesterified, or a fat containing the same. This polyhydric alcohol/fatty acid ester is capable of homogeneously dissolving a phytosterol in a large amount.

Examples of suitable polyhydric alcohol/fatty acid esters include glycerol/fatty acid esters, polyglyccrol/fatty acid esters, sucrosc/fatty acid esters, and sorbitan/fatty acid esters each having an average degree of esterification of 2 to 4.5. Preferred examples include diacylglycerols, di- and/or triacyldiglycerols, and the like because they are usable in the same manner as ordinary edible fats. Especially preferred are diacylglycerols (diglycerides), which have been found to inhibit body fat accumulation.

Diacylglycerols can be incorporated into a fat in an amount of 15% by weight or larger, preferably 30% by weight or larger, more preferably 55% by weight or larger. When a larger amount of diacylglycerols are used in combination with a phytosterol, a synergistic effect on lipid metabolism can be expected.

Diacylglycerols suitable for use in this invention are those in which the constituent fatty acids comprise $C_{8-22}$ saturated fatty acids or unsaturated fatty acids. Since the oil and fat composition of this invention can be used similarly to generally edible fats, it is preferred to use diacylglycerols in which at least 55% by weight, more preferable at least 70% by weight, of the constituent fatty acids are accounted for by unsaturated fatty acids. A larger proportion of the diacylglycerols having such unsaturated fatty acid groups are liquid at least at human body temperature, whereby a lipid metabolism effect attributable to the dissolution of a phytosterol can be expected.

The oil or fat for use in this invention is not particularly limited as long as it is a generally edible oil or fat. Within the context of the present invention, the term "oil" refers to components that are liquid at room temperature (~25° C.) and the term "fat" refers to components that are solid or semi-solid at room temperature. The generic grouping of oils and fats is referred to herein as "oil and fat", "oils and fats" or "oil/fat". Examples thereof include natural animal and vegetable oils and fats and processed fats obtained from these through transesterification, hydrogenation, fractionation, etc. Preferably used are vegetable oils such as soybean oil, rapeseed oil, rice bran oil, corn oil, and palm oil and processed fats obtained therefrom.

The phytosterol for use in the present invention is not particularly limited. Preferred examples thereof include α-sitosterol, β-sitosterol, stigmasterol, ergosterol, campesterol, α-sitostanol, β-sitostanol, stigmastanol, campestanol, etc. and their fatty acid esters, glycosides, and the like.

In the present invention, the amount of the phytosterol dissolved in the oil and fat composition is not particularly limited as long as it is in a dissolved state. From the standpoint of imparting a better cholesterol lowering effect than generally edible fats, the amount of the phytosterol dissolved in the oil and fat composition is 1.2% by weight or larger, preferably 2.0% by weight or larger, more preferably 2.5% by weight or larger.

From the standpoint of providing a fat usable equally to generally edible fats, the oil and fat composition of the present invention preferably has a smoke point of 170° C. or higher. The content of monoacylglycerols in the fat composition is preferably 2% by weight or lower, more preferably 1.5% by weight or lower.

Further, an antioxidant is preferably added to the oil and fat composition of the present invention in an amount of 50 to 2,000 ppm for the purposes of storage stability and flavor stability, as in the case of generally edible fats. The antioxidant preferably comprises one or more members selected among natural antioxidants, tocopherol, tocotrienol, ascorbyl palmitate, ascorbyl stearate, BHT, BHA, phospholipids, etc. It more preferably comprises one or more members selected among natural antioxidants, tocopherol, tocotrienol, ascorbyl palmitate, phospholipids, etc.

The oil and fat composition of the present invention can be used similarly to generally edible oils and fats and is applicable to fat-processed foods. For example, it is usable in O/W type fat-processed foods such as drinks, desserts, ice creams, dressings, toppings, mayonnaises, and sauces for grilled meat; W/O type fat-processed foods such as margarines and spreads; processed fat foods such as peanut butters, fryings, and baking shortenings; processed foods such as potato chips, snack cakes, cakes, cookies, pies, breads, and chocolates; and other foods including bakery mixes, processed meat products, frozen entrees, and frozen foods.

When the lipid ingredients contained in these foods comprise at least 15% by weight diacylglycerols and a phytosterol coexists therewith, these foods can be rendered capable of lowering the blood cholesterol level. The proportion of diacylglycerols to the phytosterol coexistent therewith in the lipid ingredients of a food is from 10 to 200, preferably from 12 to 100, more preferably from 15 to 60, in terms of diacylglycerol to phytosterol weight ratio. If the weight proportion of the phytosterols is lower than 10, no synergistic effect of coexistence can be expected even when the phytosterol is contained in a large amount. If it exceeds 200, scarcely any cholesterol lowering effect can be obtained.

It is also preferred to use the oil and fat composition of the present invention as a hypocholesteremic preparation in the form of a capsule, sugar-coated tablet, molded granules, candy, or drop.

Furthermore, it is preferred to use the oil and fat composition of the present invention as a solubilizer for phytosterols.

EXAMPLES

Having generally described this invention, a further understanding can be obtained by reference to certain specific examples which are provided herein for purposes of illustration only and are not intended to be limiting unless otherwise specified. In the Examples, the percentage is by weight unless otherwise indicated.

Examples 1 to 4 and Comparative Examples 1 and 2

Preparation of Diacylglycerols

Twenty grams of a commercial lipase preparation which was an immobilized lipase having the 1,3-position selectivity ("Lipozyme 3A"; trade name manufactured by Novo Industri A.S.) was mixed with 100 g of fatty acids obtained by decomposing rapeseed oil (fatty acid composition: 3.9% of palmitic acid, 1.7% of stearic acid, 57.0% of oleic acid, 21.9% of linoleic acid, and 12.8% of linolenic acid) and 15 g of glycerol. The mixture was reacted at 45° C. for 6 hours while the inside of the system was kept at a pressure of 5 mmHg absolute. The lipase preparation was separated from the resultant reaction mixture by filtration, and unreacted fatty acids and monoacylglycerols were separated by molecular distillation to give 72 g of purified diacylglycerols (Prepared Sample 1).

Preparation of Diacyldiglycerols

Twenty grams of the above commercial lipase preparation was mixed with 100 g of oleic acid (manufactured by Tokyo Kasei; fatty acid composition: 1.5% of palmitic acid, 2.6% of stearic acid, 89.4% of oleic acid, and 4.5% of linoleic acid) and 27 g of diglycerol (K-COL-II; trade name manufactured by Kashima Chemical). The mixture was reacted and purified in the same manner as the above to give 68 g of purified diacyldiglycerols (Prepared Sample 2).

The esterification composition of the polyhydric alcohol/fatty acid esters of each of Prepared Samples 1 and 2 is shown in Table 1.

The esterification composition was analyzed by silylating each sample with an ester-silylating agent (e.g., Silylating Agent TH, trade name manufactured by Kanto Chemical), subsequently analyzing the silylation product with a gas chromatograph equipped with a capillary column (e.g., DB™-1; trade name manufactured by J & W) and having a flame ionization detector, and determining the composition from the retention times and peak area ratios.

TABLE 1

| | Esterification Composition (%) | | | |
|---|---|---|---|---|
| | monoacyl | diacyl | triacyl | tetraacyl |
| Prepared Sample 1 (diacylglycerols) | 0.7 | 89.8 | 9.5 | — |
| Prepared Sample 2 (diacyldiglycerols) | 1.4 | 80.5 | 17.7 | 0.4 |

Prepared Sample 1 or 2 was added to purified rapeseed oil to prepare fats containing partial-esterification products in various concentrations. Further, a phytosterol ("Phytosterol"; trade name manufactured by Tama Biochemistry) was dissolved to give oil/fat composition A (Example 1), oil/fat composition B (Example 2), oil/fat composition C (Example 3; containing no purified rapeseed oil), and oil/fat composition D (Example 4) which contained the phytosterol in various concentrations. For comparison, oil/fat composition E obtained by adding only the phytosterol to purified rapeseed oil (Comparative Example 1) and oil/fat composition F obtained by adding the phytosterol and oleic acid as a solubilizer therefor to purified rapeseed oil (Comparative Example 2) were prepared. The composition and properties of each oil/fat composition and the results of evaluation for flavor as an edible fat are shown in Table 2.

in meal in an amount of 10 g per day. The blood cholesterol concentrations were measured after 14-day ingestion and 28-day ingestion. The results are shown in Table 3. Cholesterol values are expressed along with standard deviations (S.D.) obtained by statistical treatment of the data obtained.

TABLE 3

| | Initial level (mg/dl) | After 14-day ingestion (mg/dl) | After 28-day ingestion (mg/dl) |
|---|---|---|---|
| Fat composition A | 239.88 ± 14.47 | 233.13 ± 16.15 | 229.25 ± 11.41 |
| Fat composition B | 248.75 ± 18.68 | 237.13 ± 19.12 | 232.25 ± 13.59* |
| Fat composition C | 243.50 ± 14.77 | 221.00 ± 25.89** | 220.86 ± 23.07** |
| Fat composition E | 238.75 ± 15.32 | 239.63 ± 18.08 | 235.63 ± 17.61 |
| Purified rapeseed oil | 241.75 ± 15.19 | 244.13 ± 22.36 | 240.75 ± 23.10 |

Significant difference from initial level *: $p < 0.05$ **: $p < 0.01$

The groups who ingested oil/fat compositions B and C underwent a significant decrease in blood cholesterol concentration from the initial levels. In the group who ingested oil/fat composition A, a tendency to undergo a decrease in blood cholesterol concentration was observed although it was not a significant difference from the initial level. In the groups who ingested oil/fat composition E and purified

TABLE 2

| | Components (parts by weight) | 1) Content of partial esterification products having degree of esterification of 2 or higher and at least one hydroxyl group | 2) Phytosterol content | 3) Appearance | 4) Flavor |
|---|---|---|---|---|---|
| Example 1 (Fat composition A) | purified rapeseed oil + Prepared Sample 1 + phytosterol (53:45:2) | 40.1% | 1.8% | transparent | no abnormality in taste and odor |
| Example 2 (Fat composition B) | purified rapeseed oil + Prepared Sample 1 + phytosterol (32:65:3) | 59.4% | 2.8% | transparent | no abnormality in taste and odor |
| Example 3 (Fat composition C) | Prepared Sample 1 + phytosterol (95:5) | 85.1% | 4.7% | transparent | no abnormality in taste and odor |
| Example 4 (Fat composition D) | purified rapeseed oil + Prepared Sample 2 + phytosterol (25:71:4) | 70.3% | 3.7% | transparent | no abnormality in taste and odor |
| Comparative Example 1 (Fat composition E) | Purified Rapseed oil + phytosterol (97:2) | 0.8% | 2.4% | opaque | no abnormality in taste and odor |
| Comparative Example 2 (Fat composition F) | purified rapeseed oil + phytosterol + oleic acid (86:4:10) | 0.7% | 3.8% | transparent | abnormality in taste and odor |

1) By analysis with the aforementioned gas chromatograph.
2) In accordance with Standard Methods of Fat Analysis (Japan Oil Chemists' Society), 2.4.9.2 Sterol (Digitonin-bas chromatography).
3) Visual examination after storage at room temperature (25° C.) for one week.
4) Sensory comparison with commercial purified fat.

Example 5

Forty examinees each having a fasting blood cholesterol level exceeding 220 mg/dl (average blood cholesterol level: 242.5 mg/dl) were divided into five groups each consisting of eight members. Fasting blood cholesterol levels were measured on subjects who had ingested no food from 10 p.m. the previous evening to the test administration the next morning, typically a minimum of 8–10 hours. The oil/fat compositions A, B, C, and E described above and purified rapeseed oil were ingested as cooking oils by the examinees rapeseed oil, neither a significant decrease in blood cholesterol concentration from the initial level nor a tendency to undergo a decrease in the concentration was observed.

Example 6

Oil/fat compositions B, C, and F were used, after adding vitamin E in an amount of 400 ppm to each, to prepare cooking oils, which were then evaluated in cooking for fried pork cutlets. 300 g of each cooking oil was placed in a deep frying pan, and pork loin (120 g×2 pieces) having a coating consisting of egg, bread crumbs, and flour was cooked. The cooking oils were evaluated for smoking during cooking, workability, and the flavor, feeling on the tongue, and greasiness of the fried pork cutlets by five panelists in the following four grades using a commercial salad oil as a standard. The results are shown in Table 4.

Smoking
- ⊚ completely no smoking
- ○ almost no smoking
- Δ slight smoking
- x smoking Workability in cooking
- ⊚ excellent
- ○ good
- Δ slightly bad
- x bad Flavor
- ⊚ excellent
- ○ good
- Δ slightly bad
- x bad Feeling on the tongue
- ⊚ excellent
- ○ good
- Δ slightly rough
- x bad Greasiness
- ⊚ extremely light
- ○ fairly light
- Δ slightly light
- x not light at all

TABLE 4

|  | Smoking | Work-ability | Flavor | Feeling on the tongue | Greasiness |
|---|---|---|---|---|---|
| Fat composition B | ⊚ | ⊚ | ⊚ | ⊚ | ○ |
| Fat composition C | ⊚ | ⊚ | ⊚ | ⊚ | ○ |
| Fat composition F | X | X | X | Δ | ○ |
| Commercial salad oil | ⊚ | ⊚ | ⊚ | ⊚ | ○ |

The cooking oil comprising oil/fat composition F smoked considerably due to the oleic acid serving as a phytosterol solubilizer, had poor workability, and gave fried pork cutlets with a strong irritant flavor. In contrast, the cooking oils comprising oil/fat compositions B and C were usable completely equally to the commercial salad oil.

Example 7

Using oil/fat composition D, brioches were prepared according to the following recipe. The following materials excluding oil/fat composition D were weighed and mixed by means of a mixer at a low speed for 30 seconds. Thereafter, oil/fat composition D was added and the mixture was mixed for 5 minutes at a low speed and for 22 minutes at a medium speed. The obtained dough was leavened at 27° C. for 30 minutes, and low-temperature leavening was further conducted at 5° C. for 15 hours. The resultant dough was divided into 37-g portions, which were shaped into a round form after an airing time of 15 minutes. The shaped dough was leavened at 33° C. and a humidity of 75% for 60 minutes and then baked at 190° C. for 9 minutes to prepare brioches.

| (Recipe for brioche) | |
|---|---|
| Flour (hard) | 100.0 parts by weight |
| Yeast | 5.0 " |
| Yeast food | 0.1 " |
| Sugar | 15.0 " |
| Salt | 2.0 " |
| Powdered skim milk | 4.0 " |
| Whole egg | 50.0 " |
| Fat composition D | 30.0 " |
| Water | 15.0 " |

Twelve examinees each having a fasting blood cholesterol level exceeding 200 mg/dl ingested the two above-prepared brioches (about 68 g; about 10 g in terms of fat composition amount) at breakfast each day for 10 days to examine the change in blood cholesterol level. As a result, it was found that although the average blood cholesterol level (average±S.D.) of the twelve examinees at the beginning was $232.81 \pm 19.01$ mg/dl, the average blood cholesterol level thereof after 10-day ingestion was $211.53 \pm 23.49$ mg/dl. Thus, a decrease in blood cholesterol value with a clear significant difference ($p<0.05$) was observed.

Example 8

Using decomposition fatty acids obtained from a mixture of palm oil and soybean oil, diacylglycerols (Prepared Sample 3) were obtained according to the process for preparing diacylglycerols described above. (Composition of Prepared Sample 3)

| Fatty acid composition | |
|---|---|
| Palmitic acid | 19.8% |
| Stearic acid | 4.1% |
| Oleic acid | 29.1% |
| Linoleic acid | 40.1% |
| Linolenic acid | 4.9% |
| Esterification composition | |
| Monoacylglycerols | 0.4% |
| Diacylglycerols | 88.3% |
| Triacylglycerols | 11.3% |

Oil/fat composition G was prepared by compounding Prepared Sample 3, a hardened rapeseed oil (iodine value: 89, melting point: 29° C.), and a phytosterol in a weight ratio of 30:67:3.

French fried potatoes were prepared using oil/fat composition G as a shortening for frying, and evaluated. Oil/fat composition G was fed in an amount of 10 kg into a fryer and heated to 180° C. Peeled potatoes were sliced, washed with water, dried by sopping, and heated for 3 minutes in the above fryer to prepare french fried potatoes. The oil content of these french fried potatoes was about 12%.

Subsequently, these french fried potatoes were used to determine their blood cholesterol lowering effect. Eight examinees each having a fasting blood cholesterol level exceeding 200 mg/dl were caused to ingest the above-prepared french fried potatoes in an amount of 100 g (about 12 g in terms of fat composition amount) in every evening meal for 10 days to examine the change in blood cholesterol level. As a result, it was found that although the average blood cholesterol level (average+S.D.) of the eight examinees at the beginning was $233.43 \pm 17.66$ mg/dl, the average blood cholesterol level thereof after 10-day ingestion of the french fried potatoes was 219.37±20.81 mg/dl. Thus, there was a tendency for the blood cholesterol level to decrease.

The present application is based on Japanese Priority Application 10-75898, filed in the Japanese Patent Office on Mar. 24, 1998, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

We claim:

1. An oil/fat composition, comprising:
    a phytosterol dissolved in an oil/fat comprising at least one diacylglycerol, wherein
        the composition comprises 1.2% to 4.7% by weight of the phytosterol, and
        the composition comprises at least 15% by weight of the diacylglycerol.

2. The oil/fat composition as set forth in claim 1, wherein at least 55% by weight of the constituent fatty acids contained in the diacylglycerols are unsaturated fatty acids.

3. The oil/fat composition as claimed in claim 1, wherein said phytosterol is a member selected from the group consisting of α-sitosterol, β-sitosterol, stigmasterol, ergosterol, campesterol, α-sitostanol, β-sitostanol, stigmastanol, campestanol, fatty acid esters thereof and glycosides thereof.

4. The oil/fat composition as claimed in claim 1, wherein said oil/fat composition is a frying oil.

5. A food product comprising a food and the fat composition as set forth in claim 1.

6. The composition of claim 1, comprising at least 30% by weight of the diacylglycerol.

7. The composition of claim 1, comprising at least 55% by weight of the diacylglycerol.

8. The method as claimed in claim 7, wherein the phytosterol is a member selected from the group consisting of α-sitosterol, β-sitosterol, stigmasterol, ergosterol, campesterol, α-sitostanol, β-sitostanol, stigmastanol, campestanol, fatty acid esters thereof and glycosides thereof.

9. The composition of claim 1, wherein the weight ratio of the diacylglycerol to the phytosterol is 10 to 200.

10. The composition of claim 1, wherein the weight ratio of the diacylglycerol to the phytosterol is 12 to 100.

11. The composition of claim 1, wherein the weight ratio of the diacylglycerol to the phytosterol is 15 to 60.

12. A pharmaceutical composition, comprising the composition of claim 1 and a pharmaceutically acceptable carrier.

13. A method for decreasing blood cholesterol levels, comprising administering to a subject in need thereof, an effective amount of the pharmaceutical composition of claim 12.

14. A method for decreasing blood cholesterol levels, comprising administering to a subject in need thereof, an effective amount of the composition of claim 1.

* * * * *